United States Patent
Ross et al.

(10) Patent No.: US 8,069,757 B2
(45) Date of Patent: Dec. 6, 2011

(54) CAST-CUTTER

(75) Inventors: David J. Ross, Stirling (GB); George Miller, Midlothian (GB)

(73) Assignee: David J. Ross, Stirling (GB)

( * ) Notice: Subject to any disclaimer, the term of this patent is extended or adjusted under 35 U.S.C. 154(b) by 915 days.

(21) Appl. No.: 10/528,555

(22) PCT Filed: Sep. 19, 2003

(86) PCT No.: PCT/GB03/04040
§ 371 (c)(1),
(2), (4) Date: Mar. 21, 2005

(87) PCT Pub. No.: WO2004/026207
PCT Pub. Date: Apr. 1, 2004

(65) Prior Publication Data
US 2007/0144017 A1    Jun. 28, 2007

(30) Foreign Application Priority Data
Sep. 19, 2002    (GB) .................... 0221806.3

(51) Int. Cl.
*B23D 47/02* (2006.01)
*B23D 51/02* (2006.01)
*B23D 49/00* (2006.01)
*B27B 3/28* (2006.01)

(52) U.S. Cl. .............. 83/13; 83/916; 83/917; 30/370; 30/392; 30/393; 30/394

(58) Field of Classification Search .......... 83/13, 916, 83/917; 30/392, 175, 179, 181, 194, 208, 30/209, 210, 241, 278, 286, 370, 393, 394
See application file for complete search history.

(56) References Cited

U.S. PATENT DOCUMENTS

| | | | | |
|---|---|---|---|---|
| 2,015,535 A | * | 9/1935 | Sacrey | 30/272.1 |
| 2,595,841 A | * | 5/1952 | Glick et al. | 30/229 |
| 3,533,161 A | | 10/1970 | Magnin | 30/166 |
| 3,676,928 A | * | 7/1972 | Herr et al. | 30/228 |
| 3,710,445 A | * | 1/1973 | Roth | 30/241 |
| 4,106,195 A | * | 8/1978 | Berg | 30/293 |
| 4,532,707 A | * | 8/1985 | Allen | 30/200 |
| 4,577,629 A | * | 3/1986 | Martinez | 606/171 |
| 4,611,585 A | | 9/1986 | Seidle | 128/91 |
| 4,625,405 A | * | 12/1986 | Hudnutt et al. | 30/370 |
| 5,020,226 A | * | 6/1991 | Chabbert | 30/390 |
| 5,353,504 A | * | 10/1994 | Pai | 30/228 |
| 5,385,570 A | * | 1/1995 | Chin et al. | 606/170 |

(Continued)

FOREIGN PATENT DOCUMENTS

| | | |
|---|---|---|
| DE | 8415363 | 8/1984 |
| EP | 0 396 397 | 5/1990 |
| GB | 488148 | 7/1938 |

(Continued)

*Primary Examiner* — Ghassem Alie
*Assistant Examiner* — Bharat C Patel
(74) *Attorney, Agent, or Firm* — Gifford, Krass, Sprinkle, Anderson & Citkowski, P.C.

(57) ABSTRACT

A cast-cutter for use in removing a cast from a patient comprises a body (20), cutting means (18, 148, 230) supported by the body (20), and a protection member (16, 204, 206, 236, 244) supported by the body (20) and adapted to be positioned between the cutting means (18, 148, 230) and the patient, to protect the skin of the patient. In one disclosed embodiment the cutting means cuts a cast by a shearing action. In another disclosed embodiment the cutting means cuts a cast by an abrading action.

9 Claims, 15 Drawing Sheets

U.S. PATENT DOCUMENTS

| | | | |
|---|---|---|---|
| 5,457,889 A * | 10/1995 | Kimura | 30/228 |
| 5,542,182 A * | 8/1996 | Martinez | 30/179 |
| 5,673,487 A * | 10/1997 | Malagnoux | 30/179 |
| 6,308,421 B1 * | 10/2001 | Wang | 30/178 |
| 6,330,738 B1 * | 12/2001 | Yoshikawa et al. | 29/426.4 |
| 6,981,327 B2 * | 1/2006 | Nordlin | 30/360 |
| 2003/0065334 A1 * | 4/2003 | Hobgood et al. | 606/105.5 |

FOREIGN PATENT DOCUMENTS

| | | |
|---|---|---|
| GB | 633194 | 12/1949 |
| GB | 720708 | 12/1954 |
| GB | 839166 | 6/1960 |
| GB | 2 068 829 | 1/1981 |
| JP | 58130040 | 8/1983 |
| NL | 44070 | 4/1938 |

* cited by examiner

CAST-CUTTER

FIELD OF THE INVENTION

The present invention relates to a cutter, and in particular, but not exclusively, to a cutter for use in removing a cast used to immobilize an injured body part from a limb or otherwise of a patient.

BACKGROUND OF THE INVENTION

Typical "plaster" casts for use in immobilising limbs or other parts of the body are composed of a padded fibre layer surrounded by a plaster or fibre glass tape layer. Conventional cast-cutters remove such casts by cutting through the plaster or fibre glass layer, with the padded layer subsequently being cut using scissors, or other like instruments. This is normally repeated at opposing sides of the cast to enable the cast to be removed in two sections.

Conventional cast-cutters typically comprise an oscillating blade or disc which abrades or saws the plaster or fibre glass. As a result, large quantities of dust may be produced and dispersed within the air. In order to minimise the release of dust particles, a dust extraction device may be required, which may be cumbersome and adds additional expense to the cutting device.

Furthermore, conventional cutters are generally noisy in operation due to the action of the blade and a high speed motor, and the presence of the extraction device, which can be distressing, particularly to young patients. As a result, patients may become agitated, which makes removal of the cast without causing injury more difficult.

Additionally, in use, the blades of conventional cutters may become heated due to friction between the blade and the cast, which introduces the risk of burning the skin of the patient.

Due to the above problems, cast cutters which involve cutting the cast by a sawing action, even when operated by a skilled operator, may result in distress and injury to the patient.

SUMMARY OF THE INVENTION

It is among objects of embodiments of aspects of the present invention to obviate or at least mitigate the aforementioned and other problems with the prior art.

According to a first aspect of the present invention, there is provided a cast-cutter for use in removing a cast from a patient, the cast-cutter comprising:
 a body;
 cutting means supported by the body and adapted for cutting a portion of material from the cast by a shearing action; and
 a protection member supported by the body and adapted to be positioned between the cutting means and the patient, to protect the skin of the patient.

Thus, in use, the protection member may be placed adjacent or against the skin of a patient with the cutting means aligned with an end portion of the cast to be removed. Once in position, the cutting means may be activated and the cast-cutter moved along the length of the cast, with the protecting member sliding under the cast, to remove material from the cast without the possibility of causing injury to the patient.

Conveniently, the shearing action of the cast-cutter allows the cutting means to cut through the entire thickness of the cast, through both rigid and padded fibre or bandage layers, for example, eliminating the requirement for scissors or the like to cut through soft material once the rigid material has been cut using conventional methods.

However, if required, the cutting means may cut through the rigid layer only, with the padded fibre layer or bandage layers being subsequently cut using conventional scissors or the like.

Preferably, the cutting means is adapted for removing a strip of material from the cast. By cutting a strip of material from a cast by a shearing action, the noise and dust problems normally associated with rotating or oscillating blades are substantially reduced, which reduces patient discomfort and anxiety. Furthermore, because the skin of the patient is protected while the device is in use, the possibility of inadvertently causing injury thereto is minimised.

Conveniently, the cast-cutter may be used in the removal of a cast from a patient by cutting a strip from alternative, and preferably opposing sides of the cast such that the cast may be removed in two portions. Alternatively, the cast-cutter may be used to cut a single strip from a cast with the cast subsequently being spread to such an extent so as to be safely removed from the patient. In this instance, the cast-cutter is particularly advantageous in that it removes a strip of cast material of a suitable width to allow a conventional spreading tool or device to be properly and readily inserted into the gap in the cast formed by the removal of the strip. It should be noted, however, that the cast-cutter may be used to cut any number of strips from the cast, as required, to allow smooth and safe removal from the patient.

Preferably, the protection member is supported by the body via a connecting member which is coupled at one end to the body and at another end to the protection member. Conveniently, the connecting member may be adjustable in order to vary the distance between the body and the protection member in order to accommodate casts of varying thickness, for example.

Preferably, the protection member is releasably coupled to the body, allowing individual protection members formed for a specific use to be selected and coupled to the cast-cutter as required. For example, various shapes and sizes of protection members may be used with the cast-cutter in accordance with, for example, the type, size and location of the cast to be removed.

Furthermore, providing a protection member which is releasably coupled to the body allows a previously used protection member to be removed and disposed and subsequently replaced by a new, sterile protection member. In this way, the possibility of transferring infection from one patient to another is reduced. Further methods of minimising the transfer of infection between patients may involve the use of sterile covers adapted to be fitted and temporarily secured over the protection member, with a new cover being used for each patient.

Preferably, the protection member comprises a contact surface for contacting the skin of a patient when the cast-cutter is in use. Advantageously, said contact surface may be smooth in order to reduce the friction between the contact surface and the skin of a patient, allowing smoother operation and minimising discomfort experienced by the patient. The contact surface may have a substantially planar surface, or alternatively may have a slightly curved surface.

Conveniently, the protection member may comprise tapered edges in order to be smoothly guided under a cast. Additionally, tapered edges of the protection member may assist to align and guide the cast material to be cut towards the cutting means. Furthermore, providing a protection member having a tapered leading edge, at least, advantageously allows the protection member to be readily guided between the different layers of the cast material. For example, the protection member may be guided between the rigid layer and fibrous or bandage layer of a cast, thus separating any adhesion between the layers and allowing the cutting means to cut through the rigid layer only. In this case, the leading edge may be tapered on one side or alternatively on both sides of the protection member.

Preferably, the cutting means of the cast-cutter is suitable for cutting various types of casts, including plaster casts and synthetic, glass fibre casts which may comprise glass fibre tape or other similar casting material.

Conveniently, the cutting means may be adapted to cut material by a shearing action by the interaction of first and second portions, each comprising at least one cutting edge which in use cooperate to produce a shearing strain in a material positioned therebetween.

In one embodiment of the present invention, the first and second portions of the cutting means each include a single cutting edge.

Preferably, the cutting means comprises a first portion defining an aperture having a cutting edge, and a second portion having a cutting edge and adapted to be received within said aperture, such that when a section of a cast is positioned between said first and second portions, sufficient relative movement therebetween will result in a section of material being sheared from the cast by the cooperative cutting edges. For example, the first portion may define a rectangular aperture having at least two parallel cutting edges, and the second portion may have a rectangular shaped face which corresponds to the rectangular aperture in the first portion, and may have at least two parallel cutting edges for cooperation with those of the first portion.

In one embodiment of the present invention, the first portion may define two apertures each having a cutting edge, and the second portion may define two cutting elements each having a respective cutting edge and adapted to be received within a respective aperture of the first portion. Conveniently, the apertures may be elongated slots and may be aligned parallel to each other. Thus, in use, when a section of cast is positioned between the first and second portions, sufficient relative movement therebetween will result in a strip of cast material being formed between the elongated slots of the first portion and the elements of the second portion. Once the cast-cutter has been translated along the entire length of the cast, a strip from the cast will have been removed allowing the cast to be removed from the patient.

Advantageously, the first portion of the cutting means may be stationary, and the second portion may be moveable, such that in order to effect cutting of a section of a cast, the second portion is moved towards said first portion when the cast is positioned therebetween.

Conveniently, the first portion may be mounted on the protection member or may be integrally formed therewith. Alternatively, the first portion may be mounted on the connecting member which connects the protection member to the body of the cast-cutter.

Advantageously, the second portion may be mounted on the body and may be reciprocally moveable along a linear path relative to the first portion. In an alternative embodiment, the second portion may be pivotally mounted relative to the first portion and may be moved relative to the first portion along an arcuate path. Alternatively further, the second portion may be rotatably mounted relative to the first portion and may be suitably formed and arranged to shear a cast material upon rotation. Preferably, when the second portion operates by rotation, means are provided, either individually, or inte-
grally with the second portion, to assist in moving the cast-cutter along the length of the cast.

Alternatively, the first portion of the cutting means may be moveable, and the second portion may be stationary, such that a section of cast positioned between said first and second portions will be sheared by movement of the first portion towards the second portion.

Advantageously, the respective cutting edges of the first and second portions may be provided as or on separate inserts or components which are secured to the first and second portions respectively. Preferably, the inserts are releasably secured to the respective first and second portions. This arrangement is advantageous in that if a cutting edge becomes damaged or inefficient, it may be readily replaced without the need to replace the entire portion upon which the cutting edge is located. Additionally, the provision of cutting edges on separate inserts allows the first and second portions of the cutting means to be manufactured from a first material which does not have to exhibit the required mechanical properties to directly cut a cast material, which would generally be more expensive. The inserts may be manufactured from any suitable material such as plastic, ceramic or metal or the like.

In an embodiment of the present invention, the cutting means may comprise a first portion having a cutting die, and a second portion having at least one cutting edge, such that when a cast is positioned between said first and second portions, sufficient relative movement therebetween will result in a section of material located directly between the cutting edge of the second portion and the cutting die of the first portion being sheared from the cast. Conveniently, the cutting die may be mounted within the first portion and may define a spherical structure against which the cutting means engages in use. Alternatively, the cutting die may define a truncated conical structure. Advantageously, the cutting die may be loosely mounted within the first portion and be free to b translated to a small degree in at least two dimension, that is in at least one plane. This arrangement may assist in the die being self aligned with the cutting edge of the second portion when in use.

In use, the cutting means of the cast-cutter may shear discrete fragments of material from the cast, such that each cutting action of the cutting means will remove individual segments of material from a cast. Conveniently, where the cast-cutter is adapted to shear discrete fragments of material from a cast, the fragments may be passed through the second portion of the cutting means and subsequently ejected at a location removed from the point of cutting, which would assist to prevent clogging of the cutting means during use.

Alternatively, the discrete fragments removed may be ejected from below or from the rear of the cutting means. Alternatively, a continuous strip of material may be removed from the cast wherein the cutting means is adapted to progressively remove a complete strip from the length of the cast. In one embodiment of the present invention, a leading edge of the second portion of the cutting means which is received in the aperture of the first portion may be chamfered such that during a cutting action, the cast material will not be completely sheared from the cast, allowing a continuous strip of material to be removed. Alternatively, the aperture in the first portion of the cutting means may be open or chamfered at one side to prevent cutting of the cast material at that side. It should be noted that any suitable arrangement may be utilised which would prevent any shearing of the cast material in the region of one side of the first and second portions.

Alternatively, the cutting means may be adapted to remove both discrete fragments of material, and continuous strips from the cast. For example, the cast-cutter may initially be used to remove a continuous strip, which continuous strip may be terminated at any required point by the cutting means. This arrangement may be particularly advantageous for use in the removal of complex casts wherein the cast-cutter initially removes a continuous strip which is subsequently terminated to realign the cast-cutter to proceed in the removal of the cast.

Conveniently, where the cast-cutter is adapted to remove continuous strips of material from a cast, the first portion of the cutting means may comprise a strip exit to allow a strip of the cast which is being removed to pass therethrough, preventing blockage of the cutting means and assisting in efficient removal of the strip of cast material. The strip exit preferably comprises tapered sides, which sides may taper outwards, away from the aperture of the first portion. Providing the strip exit with tapered edges in this manner assists in the free movement of the strip and prevents the strip from blocking the strip exit. Additionally, the tapered edges allow the cast-cutter to more readily be operated along a curved or arcuate path.

Preferably, the cutting means is operated by electric drive means. Alternatively, the cutting means is operated by hydraulic drive means. Alternatively further, the cutting means may be operated by pneumatic drive means. It should be noted, however, that any suitable drive means may be used which would readily be selected by a person of skill in the art.

Advantageously, the cast cutter may be powered by an electrical power supply, such as a mains supply either alone or in combination with a transformer and/or a rectifier, or alternatively, or indeed additionally, by a local power supply such as a battery pack. Preferably, where the cast-cutter is powered by a battery pack, the battery pack is rechargeable. Additionally, the battery pack may be removable from the cast-cutter for recharging, replacing or disposal or otherwise.

Conveniently, the cast-cutter may be activated by depressing or otherwise closing a normally open switch, and deactivated by releasing the switch.

Preferably, the cast-cutter comprises at least one safety switch which has to be depressed or released before the main switch can be operated. This prevents the cast-cutter from being inadvertently activated by accidentally depressing the main switch.

Preferably, the cast-cutter further comprises a safety guard disposed around the cutting means to prevent accidental injury by trapping a finger, for example, while the cutter is in use. The guard may be fixed in place or alternatively may be retractable to allow access to the cutting means for cleaning or maintenance, for example. Conveniently, where the safety guard is retractable, the guard may include a safety switch such that the cast-cutter may only be operated when the safety guard is positioned correctly in place.

Preferably, the safety guard is transparent such that the cutting means may be safely viewed by a user to ensure correct operation and that a correct line of cut is being achieved.

Advantageously, the cast-cutter may further comprise means for collecting the sections of a cast which have been removed. The collecting means may comprise a container releasably attached to the body portion of the device. Alternatively, the collecting means may be a separate receptacle located remote from the cast-cutter and connected thereto by a flexible tubular member or conduit or the like.

Conveniently, the cast-cutter may comprise extraction means such as a vacuum unit which may assist in drawing the removed fragments or strips of the cast into or towards any associated collecting means.

While removing a cast from a patient using a shearing action as opposed to a sawing action will significantly reduce the amount of dust produced, it is inevitable that some dust may be created. However, the presence on an extraction means may assist to control and contain any dust produced.

Advantageously, the various components of the cast-cutter may be coated with a material to prolong service life or to allow ease of cleaning or the like. For example, a Teflon® coating may be utilised.

According to a second aspect of the present invention, there is provided a method of removing a cast from a patient, said method comprising the steps of:

providing a cast cutter having shearing cutting means and a protecting member;

placing the protecting member adjacent to the skin of the patient such that the protecting member is located between the skin of the patient and the cutting means;

aligning the cutting means with the end of the cast; and activating and moving said cast-cutter along the length of the cast to remove a strip of material therefrom, allowing the cast to be removed from the patient.

Preferably, the method further comprises the steps of:

placing the protecting member of the cast-cutter adjacent to the skin of the patient and aligning the cutting means with an alternative end portion of the cast; and activating and moving the cast-cutter along the length of the cast to allow the cast to be removed in two portions.

The above steps may be repeated as required in order to safely remove the cast from the patient.

According to a third aspect of the present invention, there is provided a cast-cutter for use in removing a cast from a patient, the cast-cutter comprising:

a body;

cutting means supported by the body and adapted for cutting a cast material by an abrasion action; and a protection member supported by the body and adapted to be positioned between the cutting means and the patient, to protect the skin of the patient.

Thus, in use, the cutting means and the protecting member may be aligned with the end of a cast and the cast-cutter subsequently activated and moved along the cast in the required cutting direction. In this way, while the cutting means abrades the cast material, the protecting means slides underneath the cast to protect the skin of the patient from injury from the cutting means.

Conveniently, the cast-cutter may be used in the removal of a cast from a patient by cutting along the length of one side of the cast or alternatively, and preferably opposing sides of the cast such that the cast may be removed in two portions. Alternatively, the cast-cutter may be used to cut along the length of a single side of the cast with the cast subsequently being spread in a conventional manner and removed from the patient.

Preferably, the cutting means includes at least one cutting disc suitably mounted on the body of the cast-cutter. The at least one cutting disc may be rotatably mounted on the body. In one embodiment of the present invention the at least one cutting disc may be rotated about an axis of rotation to effect cutting of a cast. Alternatively, the at least one cutting disc may be oscillated about an axis of rotation to effect cutting of a cast material. The cutting means may include one cutting disc. In an alternative embodiment, the cutting means may include two cutting discs mounted and movable about a common axis of rotation.

Alternatively, the cutting means may include at least one cutting rod rotatably mounted between the body and protection member, wherein the outer circumferential surface of the cutting rod is adapted in use to cut a cast material by a process of abrasion.

Advantageously, the cutting means may be driven by electric drive means such as an electric motor or the like. Alternatively, the cutting means may be driven by hydraulic or pneumatic drive means, or any other suitable drive means available in the art.

Preferably, the protection member is secured to the body of the cast-cutter by a connection member, one end of the connection member being secured or coupled to the body, and another end of the connecting member being secured or coupled to the protection member. Advantageously, the connecting member is adapted to pass through any slot or gap created in a cast material by the cutting means. In one embodiment, the connecting member may be adapted to exert a force on the walls or edges of any slot or gap through which the connection member passes, in order to force apart or spread the edges of the slot or gap. This particular feature may therefore assist in preventing the cutting means from binding or being trapped within the slot which is being cut, allowing for improved and easier operation.

Conveniently, a single connection member may be provided. Alternatively, two or more connecting members may be provided, wherein each connecting member is adapted to pass through a respective slot or gap created in a cast material by the cutting means. Thus, where the cutting means comprises two cutting discs, for example, there may be provided two connecting members.

Advantageously, the protection member may be pivotally mounted on the body of the cast-cutter. In this way, relative movement between the cutting means and the protection member may be achieved, allowing the cast-cutter to be effectively utilised on casts of varying thickness. Additionally, the cutting means may be removed from the particular slot being formed or cut in the cast while maintaining the protection member under the cast. In this way, the cutting means may be retracted from the cast material for inspection, cleaning or replacement or the like, without having to withdraw the protecting member from under the cast.

The cast-cutter according to the third aspect may comprise various preferred and optional features such as those described above with reference to and in accordance with the first aspect of the present invention. Thus, for the purposes of brevity, these preferred and optional features have not been repeated.

According to a fourth aspect of the present invention, there is provided a method of removing a cast from a patient, said method comprising the steps of:

providing a cast cutter having abrading cutting means and a protecting member;

placing the protecting member adjacent to the skin of the patient such that the protecting member is located between the skin of the patient and the cutting means;

aligning the cutting means with an end of the cast; and activating and moving the cast-cutter along the length of the cast to cut through the cast, allowing the cast to be removed from the patient.

The cast may be cut any number of times by the cast-cutter in order to safely remove the cast from the patient.

BRIEF DESCRIPTION OF THE DRAWINGS

These and other aspects of the present invention will now be described, by way of example only, with reference to the accompanying drawings, in which.

DETAILED DESCRIPTION OF THE INVENTION

Figure 1:
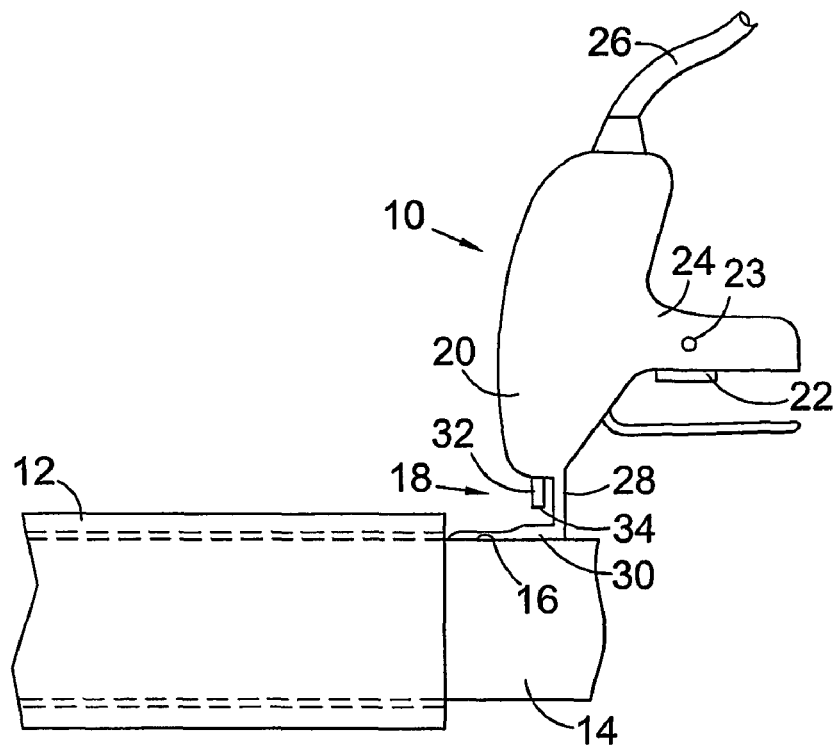
FIG. 1 shows a cast-cutter in accordance with an embodiment of the present invention.

Reference is first made to FIG. 1 of the drawings in which there is shown a cast-cutter 10 in accordance with one embodiment of the present invention. The cast-cutter 10 is shown in use removing a cast 12 from a body part 14 of a patient. The cast-cutter 10 comprises a protective shoe 16 and cutting means 18 which are both supported by a body portion 20 of the cast-cutter 10. As shown, the protective shoe 16 is positioned between the cutting means 18 and the body part 14, thus protecting the patient from injury during operation.

The cast-cutter 10 further comprises a main switch 22 and a safety switch 23, both located on a handle 24, said switches 22, 23 for activating the cutting means 18. In the embodiment shown, the cast-cutter 10 is operated by electric drive means and is provided with electrical energy via electrical cable 26. As shown, the handle 24 is aligned with the intended direction of cut which provides a user with improved control when using the cast-cutter 10.

As shown in FIG. 1, the protective shoe is supported by the body portion via a connecting member 28 which is coupled at one end to the body portion 20 and at another end to the protective shoe 16.

Figure 18:
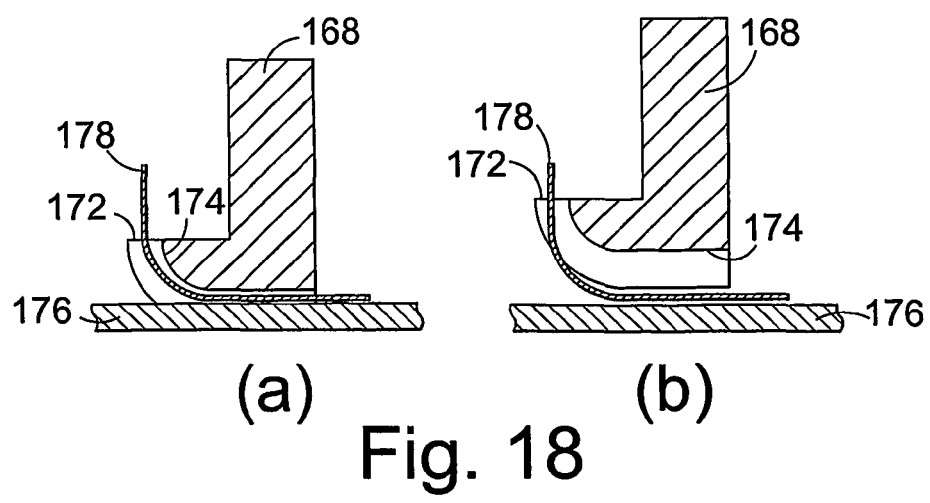
FIG. 18A shows a strip of cast material trapped within a channel.
FIG. 18B shows a strip of cast material released from a channel.

In use, the protective shoe 16 may be placed against the skin of the patient's body part 14 with the cutting means 18 aligned with an end portion of the cast 12. Once in position, the cutting means 18 is activated by depressing switch 22, in combination with the safety switch 23, and the cast-cutter 10 is moved along the length of the cast 12, with the protective shoe sliding under the cast 12, to remove a strip of material therefrom without the possibility of the cutting means 18 causing injury to the patient. The cast-cutter 10 preferably includes a safety guard as described hereinafter with reference to FIG. 18.

The cutting means 18 shown in FIG. 1 effects cutting of the cast 12 by a shearing action. In the embodiment shown, the cutting means 18 comprises a first, fixed portion 30 formed integrally with the protective shoe 16, and a second portion 32 reciprocally mounted on the body portion 20 of the cast-cutter 10. The fixed portion 30 defines an aperture 38 (FIG. 2) having a cutting edge 39 (FIG. 2), which aperture 38 is adapted to receive a cutting edge 34 of the second portion 32 of the cutting means 18. Thus, when a cast 12 is positioned between the first and second portions 30, 32 of the cutting means 18, and the cutting means 18 is activated, interaction between the cutting edge 34 of the second portion 32 with the cutting edge 39 of the aperture 38 in the fixed portion 30 will result in a section of the cast being sheared therefrom. Thus, the reciprocating motion of the second portion 32 of the cutting means 18 in combination with the advancing movement of the cast-cutter 10 along the length of the cast 12 will result in a strip of the cast being removed.

A detailed description of various embodiments of the cutting means 18 of the present invention will now be described with reference to FIG. 2 to 14.

Figure 2:
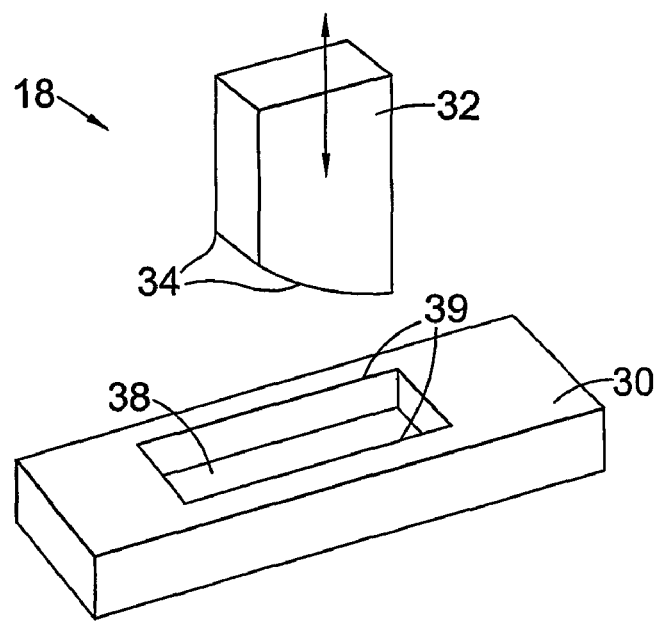
FIG. 2 is a simplified perspective view of the cutting means of the present invention.

Referring initially to FIG. 2, there is shown a simplified perspective view of the cutting means 18 of a cast-cutter in accordance with an embodiment of the present invention. The cutting means 18 comprises a fixed, first portion 30 defining a rectangular aperture 38 having two parallel cutting edges 39, the fixed portion 30 adapted for receiving a second portion 32 having a generally rectangular shaped face which corresponds to the rectangular aperture 38 in the first portion 30, and has two parallel cutting edges 34 for cooperation with the cutting edges 39 of the first portion. The second portion 32 is reciprocally mounted on the cast-cutter (not shown) and will cut a portion of material from the cast on a down-stroke. It should be noted that the term "down-stroke" used in this context relates to the direction of movement of the second portion 32 with respect to the orientation of the representation. However, in more general terms, down-stroke should be understood to mean a stroke of the second portion 32 in an outward direction relative to the body of the cast-cutter. Thus, a section of material which is sheared from the cast will be ejected from below the fixed portion 30.

Figure 3:
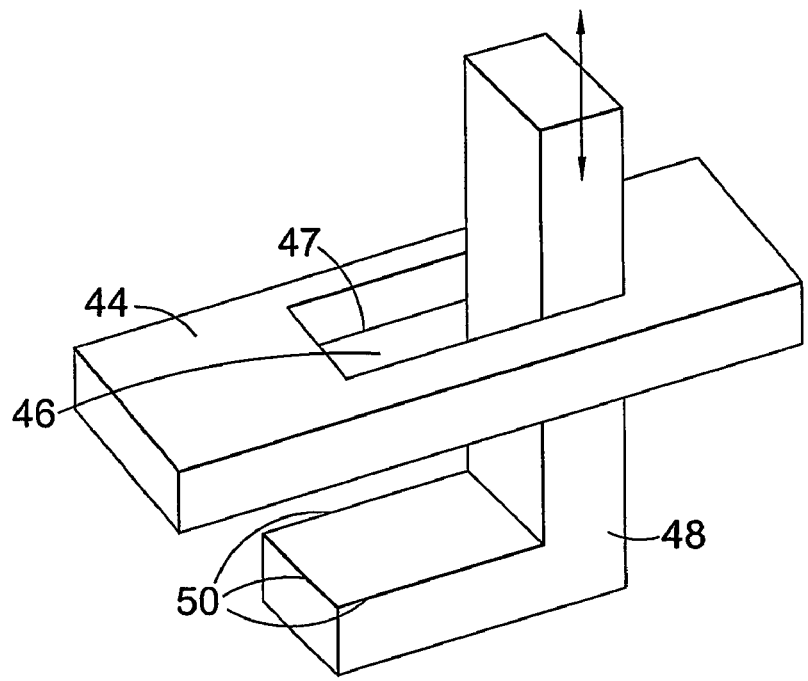
FIG. 3 shows an alternative embodiment of the cutting means of the present invention.

Referring now to FIG. 3, an alternative cutting means will be described. As in the embodiment shown in FIG. 2, the cutting means comprises a fixed portion 44 defining an aperture 46 having cutting edges 47 (only one shown), within which aperture 46 is received a moveable portion 48 which is reciprocally mounted on the cast-cutter. The moveable portion 48 includes cutting edges 50, which cutting edges cooperate with the cutting edges 47 of the aperture 46 to shear material from the cast being removed. In the embodiment shown in FIG. 3, the moveable member 48 cuts the cast on its upstroke, and ejects the sheared section of cast from above the aperture 46 in the fixed portion 44.

Figure 4:
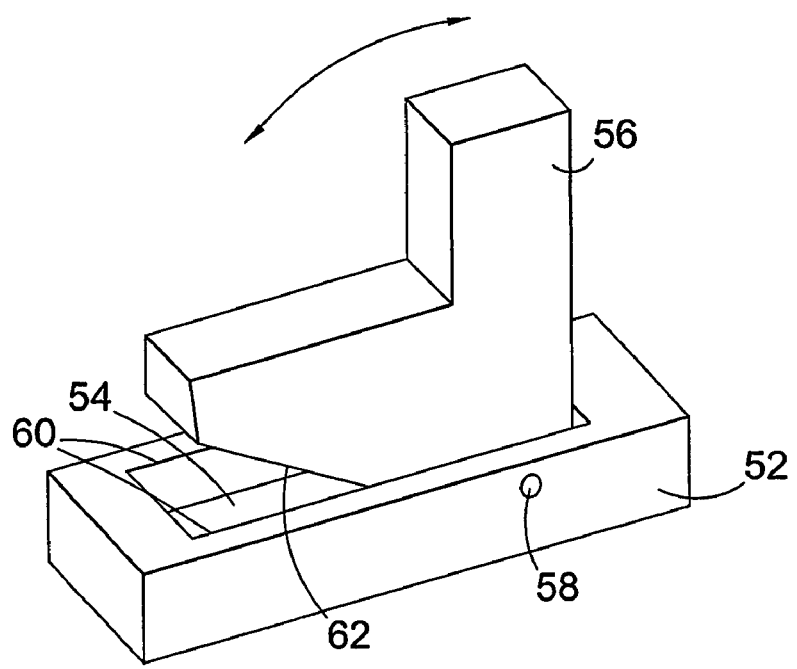
FIG. 4 shows a further alternative embodiment of the cutting means of the present invention.

A further arrangement is represented in FIG. 4 wherein a cutting means is shown which comprises a stationary first portion 52 having an aperture 54, and a moveable second portion 56 which is pivotally mounted in said aperture 54 via pivot pin 58. In use, a portion of a cast to be removed is positioned between the first and second portions 52, 56 and the moveable portion 56 is pivoted within said aperture 54, such that the cast is sheared by respective cutting edges 60, 62 of the aperture 54 and the second portion 56. As with the embodiment shown in FIG. 2, the sheared cast portion is ejected from below the first portion 52.

Figure 5:
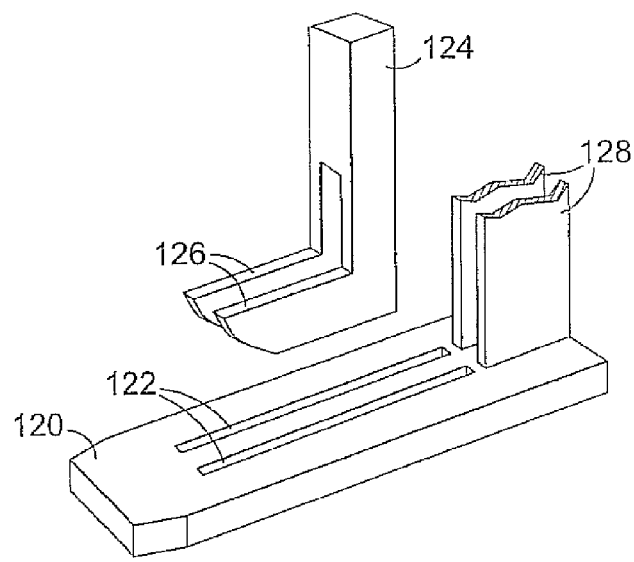
FIG. 5 shows yet a further alternative embodiment of the cutting means of the present invention.

A still further arrangement is shown in FIG. 5 in which a cutting means is shown which comprises a stationary first portion 120 defining two elongated apertures or slots 122, and a moveable second portion 124 which is reciprocally mounted on the body (not shown) of the cast-cutter. The second portion 124 comprises two cutting extension 126 extending from the lower end thereof, wherein the cutting extension 126 are each adapted to be received within a respective slot 122. Thus, when a cast material is located between the first and second portions 120, 124 of the cutting means shown in FIG. 5, and the cutting means is activated, the cutting means will cut through the cast. In this way, a strip of cast material will be formed between the cutting extensions 126.

The first portion is secured to the body (not shown) of the cast cutter by two connecting members 128 positioned adjacent each other and spaced apart by at least the same distance as the slots 122. This arrangement allows any strip of cast material formed by the cutting means to pass between the connecting members 128 and subsequently be removed without causing any blockage.

Figure 6A:
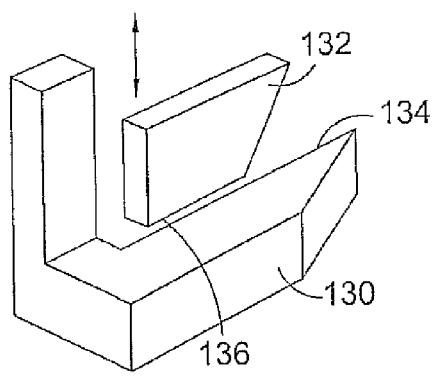
FIG. 6A depicts a cuttings means with moveable portion which reciprocates relative to a stationary portion.
Figure 6B:
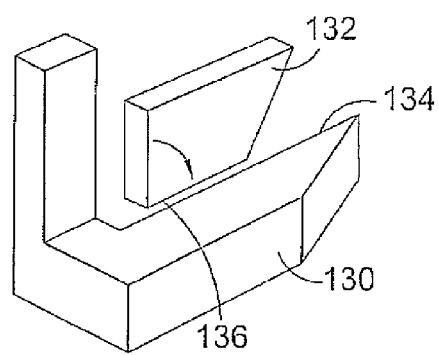
FIG. 6B depicts a cuttings means with moveable portion which pivots relative to a stationary portion.

Referring to FIG. 6, an alternative cutting means will now be described. The cutting means shown includes a first, stationary portion 130 supported by the body (not shown) of the cast-cutter, and a second, moveable portion 132 which is mounted on the body of the cast-cutter and is adapted to either reciprocate (FIG. 6A) and/or pivot (FIG. 6B) with respect to the stationary portion 130. In the embodiment shown in FIGS. 6A and 6B, the first portion 130 defines a single cutting edge 134, and the second portion 132 also defines a single cutting edge 136 corresponding to, and aligned with cutting edge 134 of the first portion 130. In use, cutting edges 134, 136 cooperate to cut a cast material located therebetween.

Figure 7:
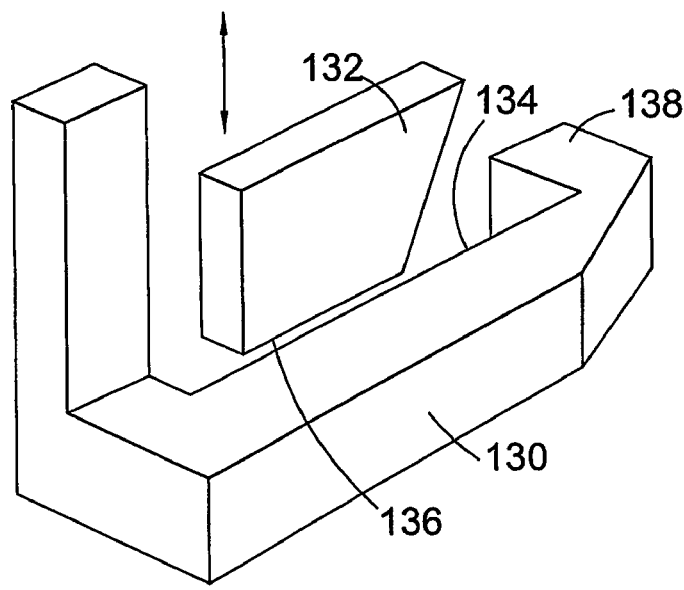
FIG. 7 shows a cutting means with a front extension or guard.

A similar arrangement to that shown in FIG. 6 is shown in FIG. 7, and as such like components share like reference numerals. The structure and operation of the cutting means shown in FIGS. 6 and 7 is similar, with the exception that the first, stationary portion 130 shown in FIG. 7 includes a front extension or guard 138. In use, the front guard 138 prevents a patient's skin, for example, from becoming trapped between the cutting edges 134, 136 of the first and second portions 130, 132 respectively.

Figure 8:
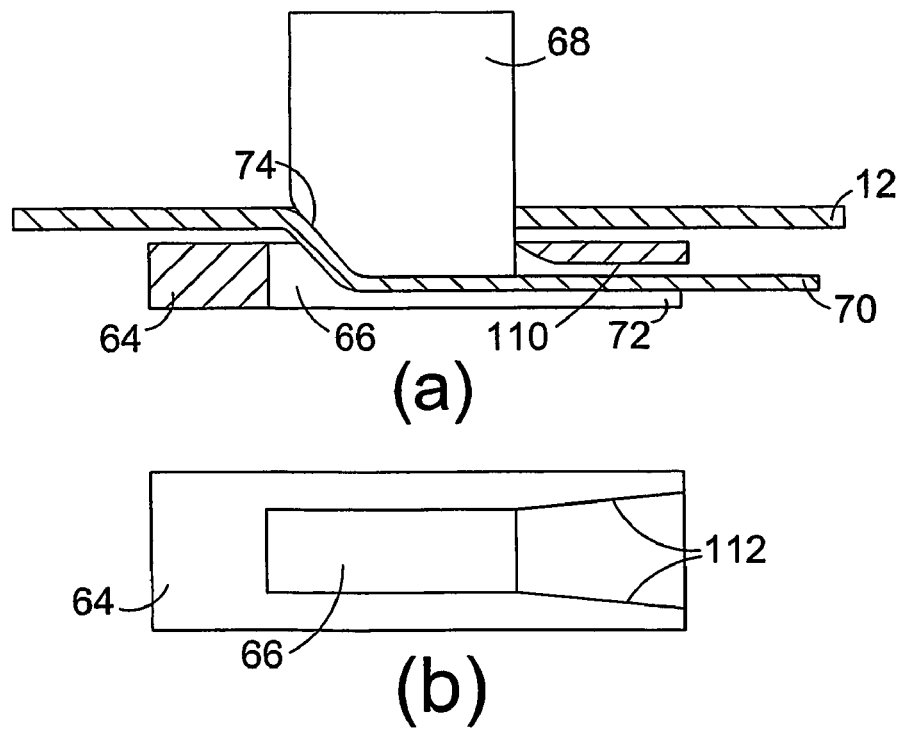
FIG. 8A is a cross-sectional side view of a cutting means of a cast cutter.
FIG. 8B is a bottom view of the cutting means of FIG. 8A.

Reference is now made to FIGS. 8(*a*) and (*b*) in which there is shown a cross-sectional side view and a bottom view respectively of a cutting means of a cast-cutter in accordance with one embodiment of the present invention. The cutting means 18 is similar to that shown in FIG. 2 in that it comprises a fixed first portion 64 defining an aperture 66 for receiving a second moving portion 68. The cutting means 18 shown in FIG. 8 is adapted for cutting a strip 70 of material from a cast 12, wherein the strip 70 is ejected from the fixed portion 64 through a strip exit 72. The leading edge of the second portion 68 is chamfered 74 such that during a cutting action, the cast material will not be completely sheared from the cast, allowing a continuous strip 70 to be removed. It should be noted that the term "continuous" as used above implies that during a cutting action of the cutting means 18, a portion of the strip 70 being removed remains attached to the cast 12. However, the cutting means 18 may be adapted to completely shear the strip 70 from the cast 12, for example, when it is required to terminate the strip 70 to remove the cast-cutter or to change the direction of the cast-cutter.

The upper 110 and side walls 112 of the strip exit 72 are outwardly tapered to allow the cast-cutter to readily be moved in an arcuate or curved path when in use, and also to prevent the strip 70 from blocking the strip exit 72.

Figure 9:
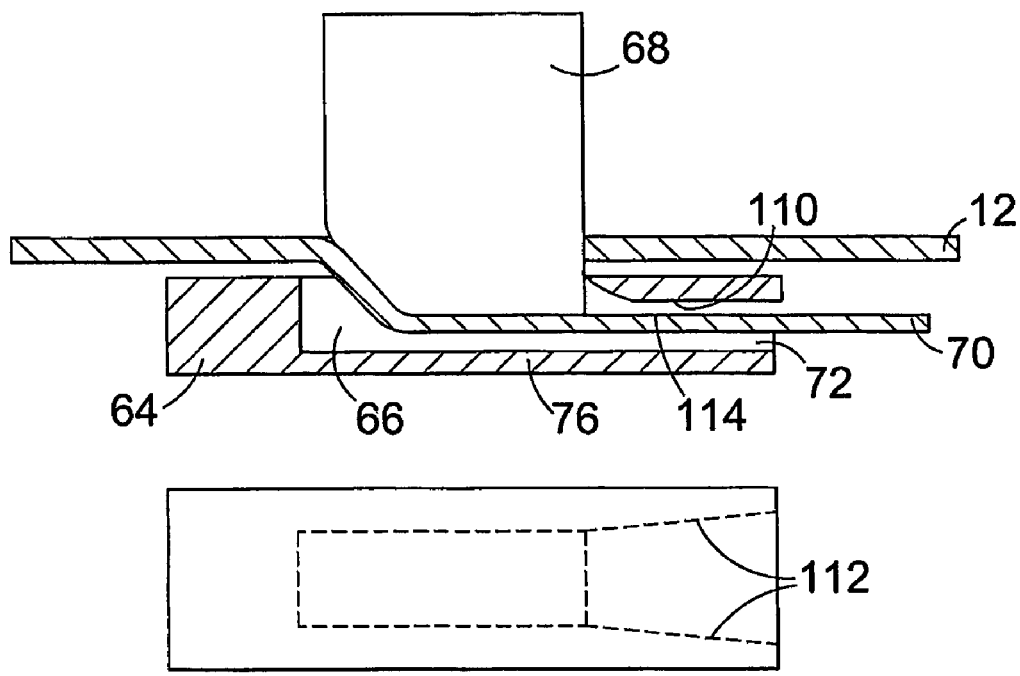
FIG. 9 shows a cutting means with a floor portion.

A similar embodiment to that shown in FIG. 8 is shown in FIG. 9, the difference being the existence of a floor portion 76 which closes the underside of the aperture 66 in the fixed portion 64. The floor portion 76 guides the strip 70 towards the strip exit 72 and when the fixed portion is mounted on, or forms part of the protective shoe, the floor portion 76 prevents the sheared cast material from being ejected towards and against the skin of the patient. Additionally, the floor portion may also provide a barrier between the second, moveable member 68 and the patient's skin.

The upper 110, lower 114 and side walls 112 of the strip exit 72 of the embodiment shown in FIG. 9 are outwardly tapered for the same reasons as discussed above with reference to FIG. 8.

Figure 10:
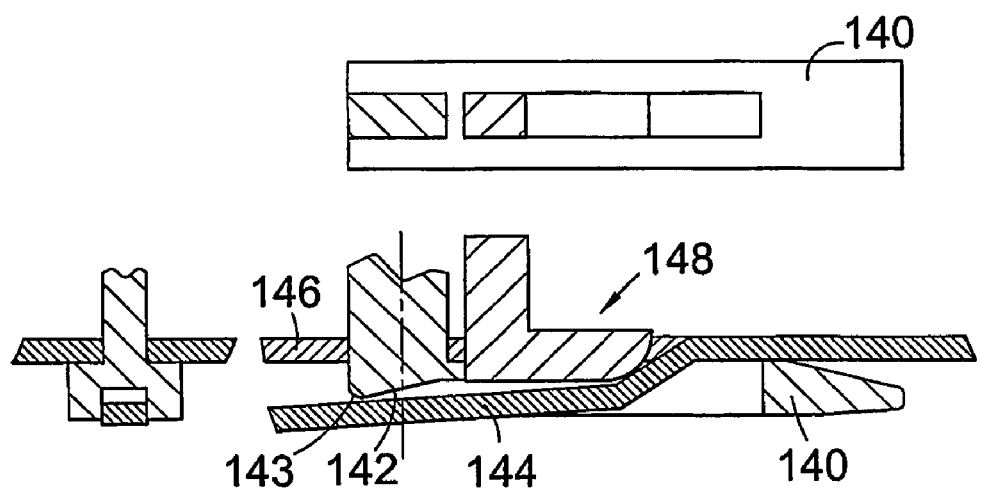
FIG. 10 includes a downwardly tapered rear surface to assist in moving a strip removed from a cast away from the cutting means.

FIG. 10 shows a similar arrangement to that of FIGS. 8 and 9. However, the fixed portion, identified as numeral 140 in FIG. 10 includes a downwardly tapered rear surface 142 to assist in moving a strip 144 removed from the cast 146 away from the cutting means, generally indicated by reference numeral 148. As shown, the rear edge 143 if the tapered surface is rounded to prevent catching on the cast material being removed, or alternatively to prevent catching or snagging when the cast-cutter and thus stationary portion 140 is retracted from under the cast 146.

Figure 11:
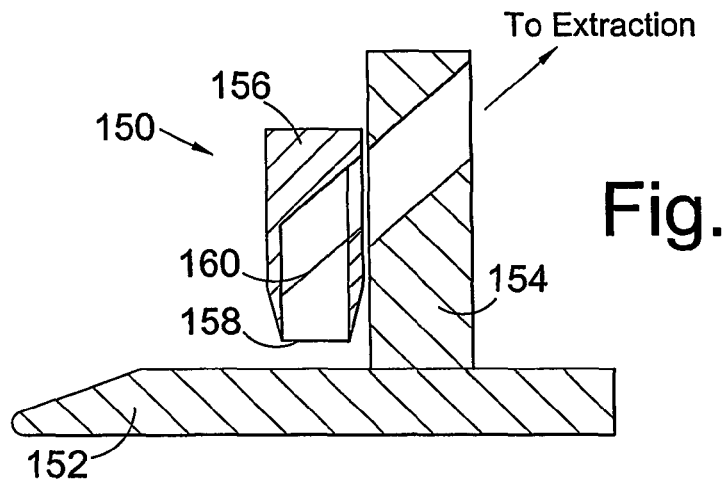
FIG. 11 is a cross-sectional diagrammatic representation of a cutting means embodiment of the present invention.
Figure 12:
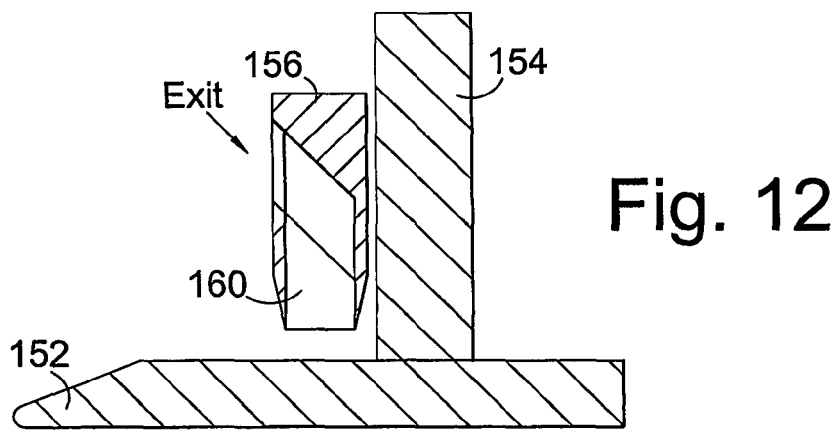
FIG. 12 shows how material may exit from the front of the second portion of the cutting means.

Reference is now made to FIG. 11 in which there is shown a cross-sectional diagrammatic representation of a cutting means 150 in accordance with an embodiment of the present invention. The cutting means 150 is specifically adapted to remove discrete segments from a cast and comprises a first portion 152 fixed to the body (not shown) of the cast-cutter via a connection member 154, and a second portion 156 reciprocally mounted on the body of the cast-cutter. The second portion defines a cutting edge 158 and an internal bore 160. In use, a portion of a cast material located between the first and second portions 152, 156 is cut and is forced inside the bore 160 of the second portion 156. As cutting of the cast continues, each new portion removed from the cast will be forced inside the bore 160, resulting in existing cast material being forced further into the bore 160. In this way, the material cut from the cast may be forced away from the cutting means 150 towards a point of extraction or collection. In FIG. 11, the material cut from the cast will exit from the rear of the second portion. However, the material may exit from the front of the second portion as shown in FIG. 12. The extraction process may be assisted by a vacuum device (not shown) adapted to draw the cast portions removed from the cast upwards through the bore 160 of the second portion 156.

Figure 13:
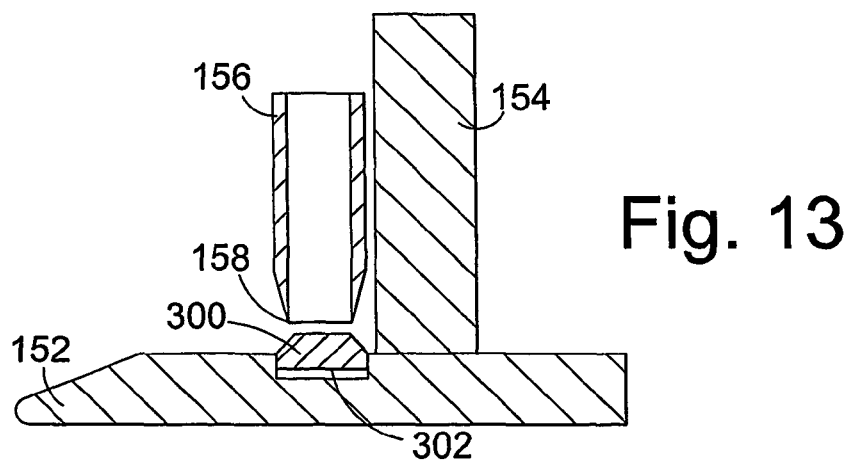
FIG. 13 depicts a first portion with a cutting die mounted therein.

A similar embodiment to that shown in FIG. 11 is shown in FIG. 13, wherein like components share like reference numerals. In this embodiment, the first portion 152 includes a cutting die 300 mounted therein. The cutting die 300 incorporates a truncated conical structure which is adapted to cooperate with the cutting edge 158 to shear a cast material. The cutting die 300 is loosely mounted within the first portion 152 such that it may be aligned with the cutting edge 158 of the second portion 156. Additionally, a gap 302 is provided beneath the cutting die 300 in order to allow the cutting die 300 to be depressed into the first portion 152. Although not specifically shown, the gap 302 is preferably provided with a resilient member in order to provide the cutting die 300 with shock absorption means to prevent damage thereto from prolonged use.

Figure 14:
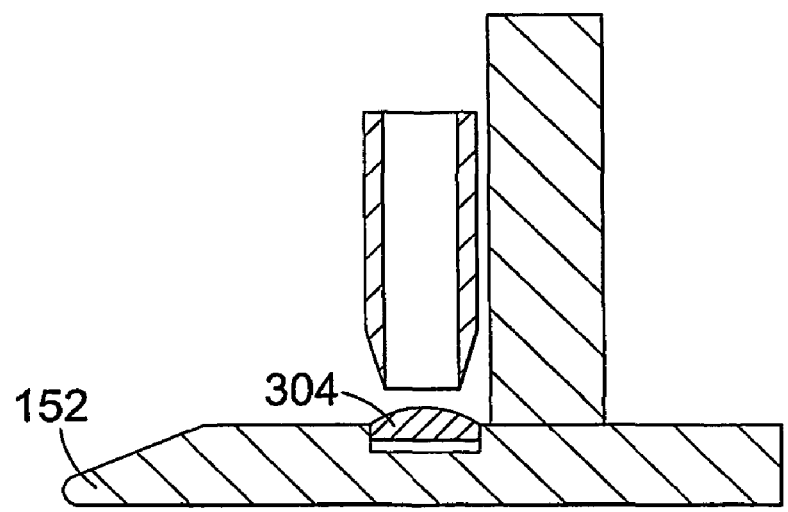
FIG. 14 shows a cutting die mounted within the first member.

A similar embodiment is shown in FIG. 14 wherein a cutting die 304 is provided mounted within the first member 152, wherein the cutting die 304 defines a domed or spherical structure.

Figure 15:
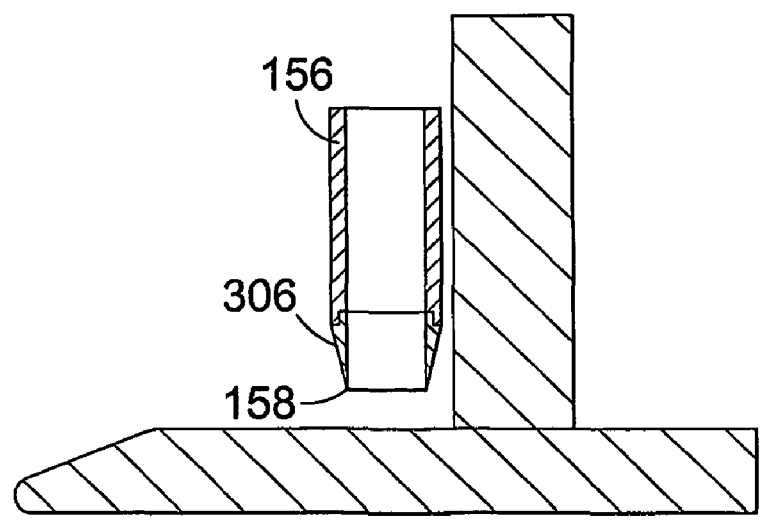
FIG. 15 shows the cutting edge of the second portion on a removable tip portion.

Referring now to FIG. 15, there is shown another similar embodiment to that of FIG. 11. In this embodiment, the cutting edge 158 of the second portion 156 is provided on a removable tip portion 306, such that the tip portion 306 may be readily replaced when the cutting edge 158 becomes worn.

Figure 16:
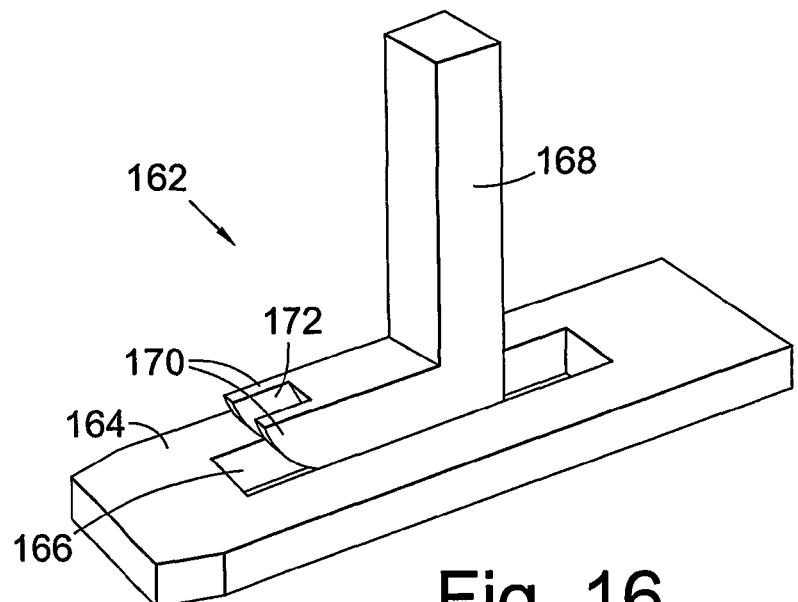
FIG. 16 illustrates a fixed first portion defining an aperture and a reciprocating second portion having two parallel cutting extensions which cooperate with the aperture in the first portion to cut a cast material.
Figure 17:
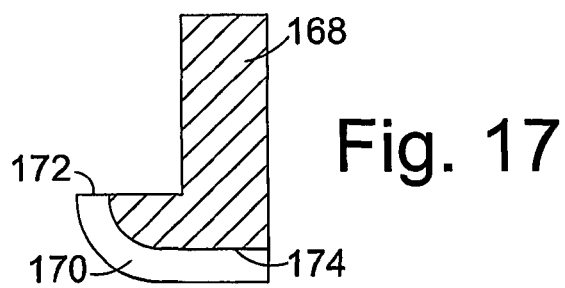
FIG. 17 is a cross-sectional view of the form of the second portion shown in FIG. 16.

A cutting means 162 according to an alternative embodiment of the present invention is shown in FIG. 16, and comprises a fixed first portion 164 defining an aperture 166, and a reciprocating second portion 168 having two parallel cutting extensions 170 which cooperate with the aperture 166 in the first portion 164 to cut a cast material. As shown, the second portion 168 includes a relief 172. The form of the second portion is shown in the cross-sectional view of FIG. 17, wherein a channel 174 is defined between the cutting extensions 170 (only one shown in FIG. 17). This particular form of the second portion 168 is advantageous in that the force exerted on the cast by the cutting means 162 as a whole will be maximised in the required region of cut, that is, in the region around the edge of aperture 166.

The relief 172 in the second portion allows access into the channel 174 to dislodge any cast material which may have become trapped therein, as represented in FIGS. 18(a) and (b). In FIG. 18(a), a strip of cast material 176 is shown trapped within the channel 174. However, the presence of relief 172 allows a dislodging device 178 to by forced into the channel 174 to release the strip 176, as shown in FIG. 18(b).

Figure 19:
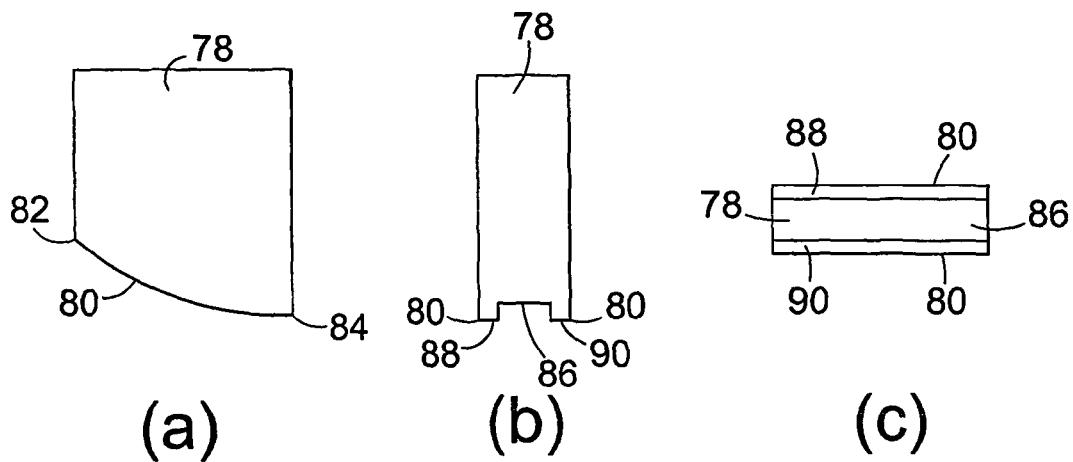
FIG. 19A is a side view of cutting means for use in the cast-cutter shown in FIG. 1.
FIG. 19B is a front view of cutting means shown in FIG. 19A.
FIG. 19C is a bottom view of cutting means shown in FIG. 19A.

Various alternative forms of moveable second portions of cutting means for use on a cast-cutter of the present invention will now be described with reference to FIGS. 19 to 21. Referring first to FIGS. 19(a) to (c), there is shown side, rear and bottom views respectively of a moveable portion 78. The moveable portion 78 includes curved cutting edges 80 which curve downwards from a leading edge 82 to a trailing edge 84 of the moveable portion 78. As shown more clearly in FIGS. 19(b) and (c), the moveable portion comprises a channel 86 located between the cutting edges 80, such that, in use, the area of the contact surfaces 88, 90 is reduced which increases the cutting pressure which is exerted on the cast by the moveable member 78. Additionally, the contact surfaces 88, 90 assist in preventing the cast material from slipping during a cutting action.

Figure 20:
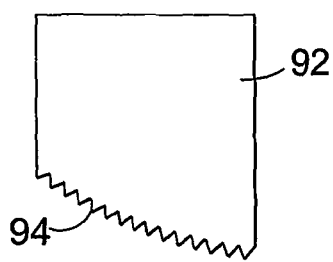
FIG. 20 shows a cutting edge which is serrated, such that, when in use, a number of contact points are created, which provides for improved gripping of the cast material and improved mechanical cutting properties.

An alternative moveable member 92 is shown in FIG. 20. In this embodiment, the cutting edge 94 is serrated, such that, when in use, a number of contact points are created, which provides for improved gripping of the cast material and improved mechanical cutting properties. For example, the cutting force imparted by the cast-cutter will be distributed by point loading onto the cast material, which will maximise the cutting pressure exerted on the cast and will better induce crack propagation, particularly in rigid cast material.

Figure 21:
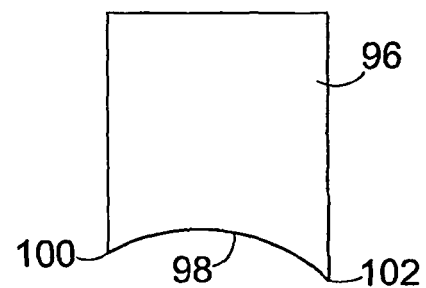
FIG. 21 depicts a further alternative embodiment of the invention wherein the cutting edge of the moveable member is curved in an arch profile between leading and trailing edges of the moveable portion.

A further alternative embodiment is shown in FIG. 21, wherein the cutting edge 98 of the moveable member 96 is curved in an arch profile between leading 100 and trailing 102 edges of the moveable portion. This particular form of moveable member 96 is advantageous particularly in the removal of individual discrete portions of the cast material, as opposed to complete strips, as cutting will be effected initially from the leading and trailing edges 100, 102, and then progressively by the side edges of the member 96 towards its centre, and will again maximise the cutting pressure. Although not apparent from FIG. 21, the moveable member 96 may have a similar channel to that channel 86 shown in FIGS. 19(b) and (c). Again, the specific shape of the moveable portion 96 will assist in gripping the cast material when the cast cutter is in use.

Figure 22:
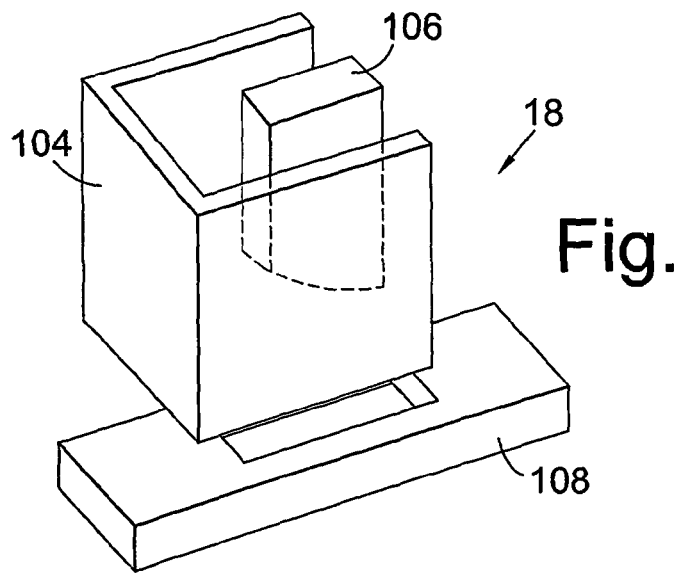
FIG. 22 shows a perspective view of a safety guard for use with the cast-cutter shown in FIG. 1.

Reference is now made to FIG. 22 in which there is shown a simplified perspective view of cutting means of the present invention including a safety guard 104 located around the moveable member 106, and above the fixed member 108. In use, the guard 104 is moved into place in order to prevent injury by trapping a finger or the like and to prevent portions of cast material being discharged from the cutting means. The safety guard 104 includes an additional safety switch (not shown), which only allows the cast-cutter to be operated when the guard 104 is securely and properly located in its guarding position. Additionally, the safety guard 104 is manufactured of a substantially transparent material such the cutting means may be viewed when the cast-cutter is in use.

Further alternative embodiments of cutting means of the cast-cutter according to the present invention will now be described with reference to FIGS. 23 to 26. As with previous described embodiments, the cutting means includes a stationary portion and a moveable portion, and as such in the embodiments shown in FIGS. 23 to 26, the stationary portion will be identified with reference numeral 180, and the moveable member with numeral 182.

Figure 23:
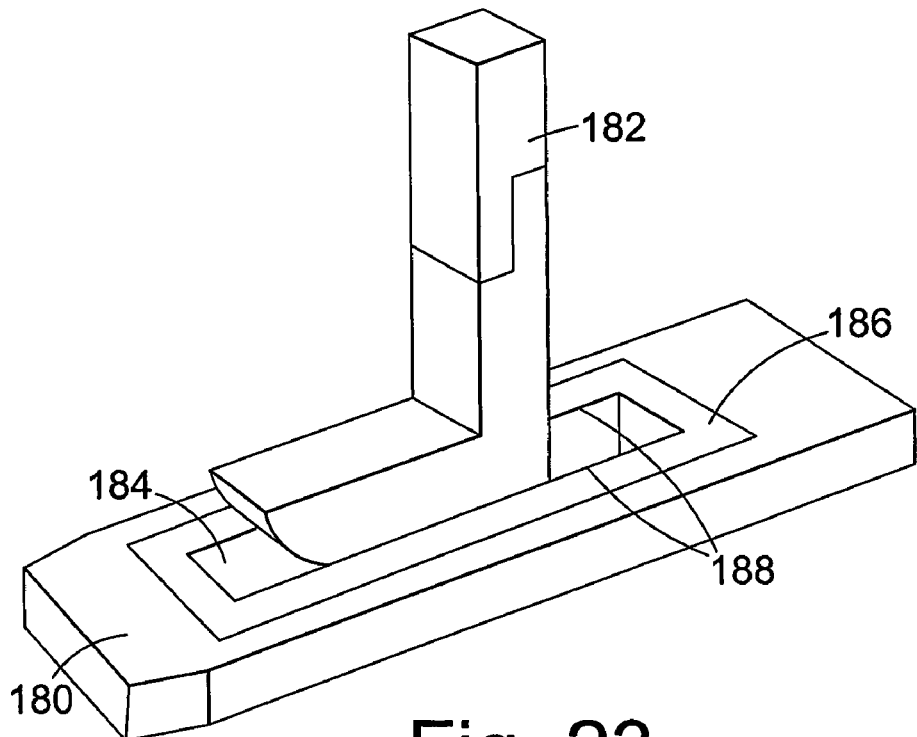
FIG. 23 shows a further alternative embodiment of cutting means of a cast-cutter according to an aspect of the present invention.
Figure 24:
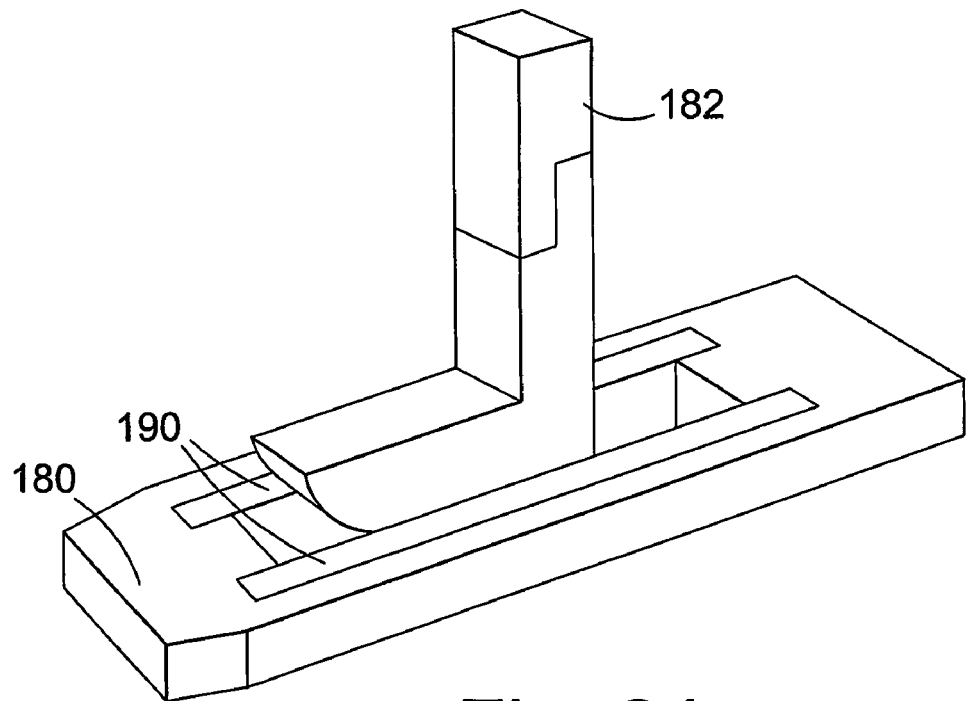
FIG. 24 shows two separate inserts provided in a stationary member.
Figure 25:
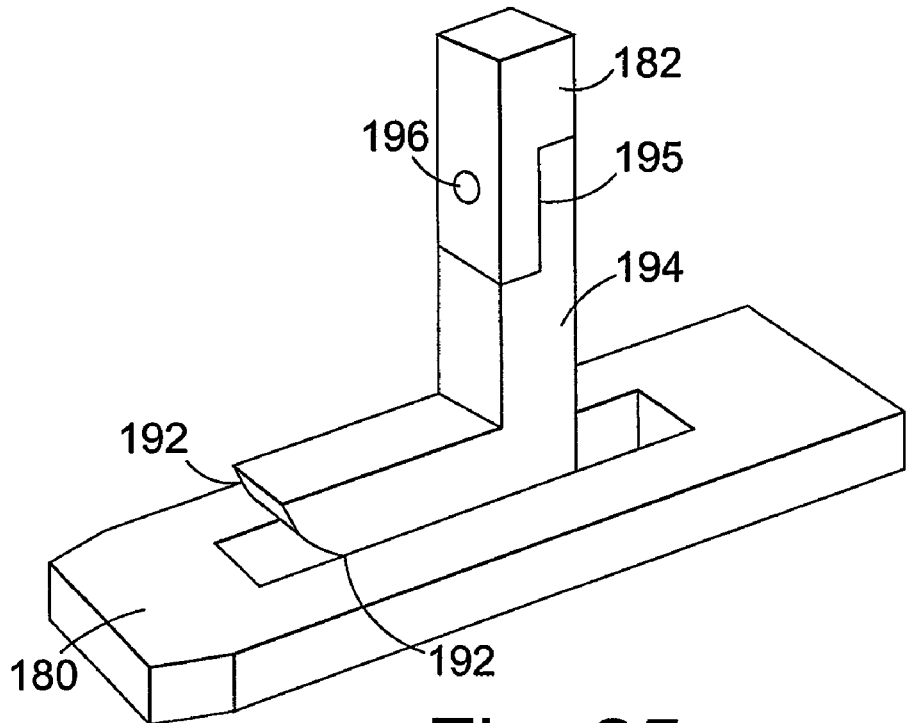
FIG. 25 shows a moveable portion defining cutting edges which are provided on a removable cutting extension which is secured to the moveable portion.
Figure 26:
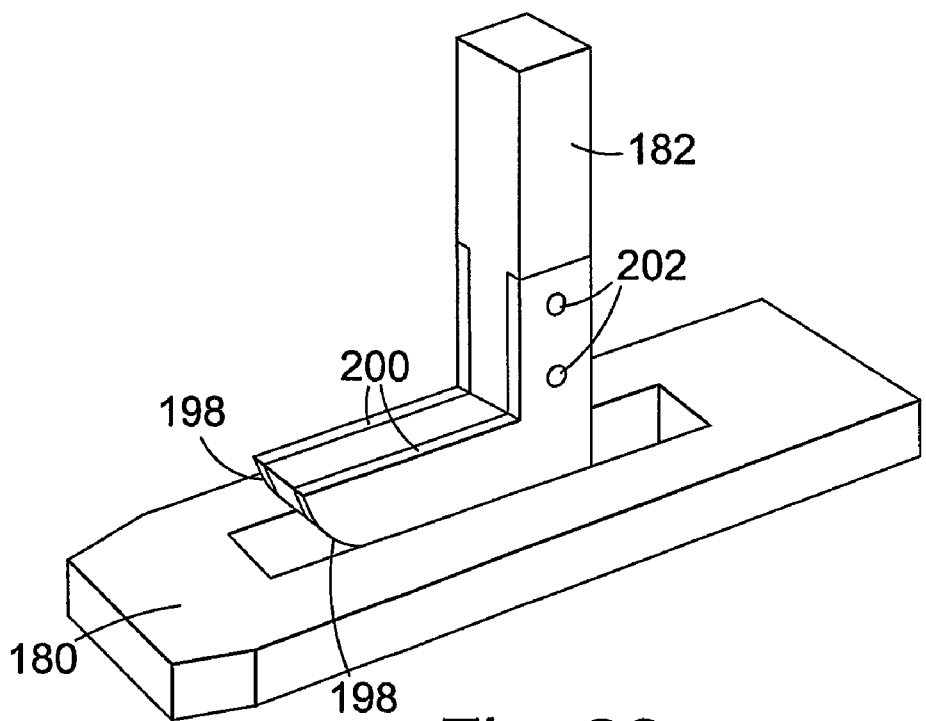
FIG. 26 shows cutting edges provided on two separate cutting extensions which are secured by suitable fixings to a moveable portion 182.

Referring initially to FIG. 23, the stationary member 180 comprises an aperture 184 defined by an insert 186 which incorporates cutting edges 188. When the cutting edges 188 become worn, the insert 186 may be removed and replaced, without having to replace the entire stationary portion 180. A similar arrangement is shown in FIG. 24, wherein two separate inserts 190 are provided in the stationary member 180. Referring now to FIG. 25, the moveable portion 182 defines cutting edges 192 which are provided on a removable cutting extension 194 which is secured to the moveable portion 182, in the embodiment shown by a locating profile 195 and a suitable fixing 196. Thus, as the cutting edges 192 become worn, the cutting extension 194 may be readily replaced without having to replace the entire moveable portion 182. A similar arrangement is shown in FIG. 26 wherein cutting edges 198 are provided on two separate cutting extensions 200 which are secured by suitable fixings 202 to the moveable portion 182.

Figure 27:
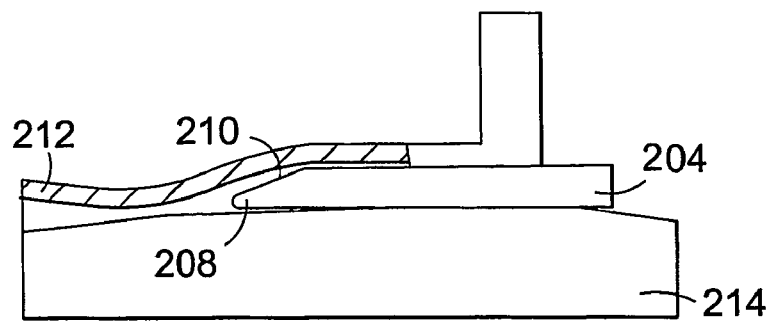
FIG. 27 shows an alternative embodiment of a protective shoe of a cast-cutter according to the present invention.
Figure 28:
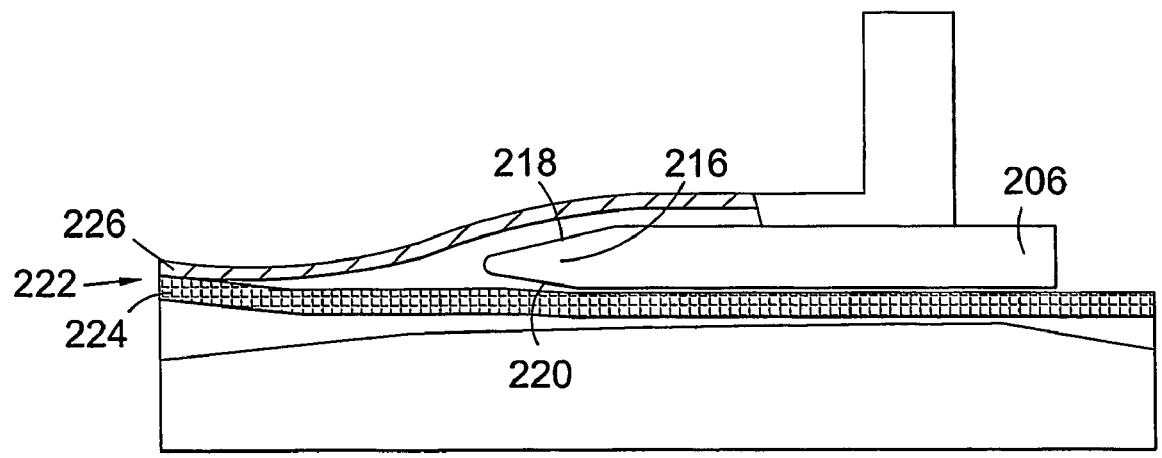
FIG. 28 shows the protective shoe of FIG. 27 incorporating a profiled nose.

Referring now to FIGS. 27 and 28 there is shown two alternative forms of a protective shoe 204, 206 respectively, in accordance with embodiments of the present invention. The protective shoe 204 shown in FIG. 27 incorporates a profiled nose 208 having an upper tapered surface 210. In use, the tapered surface 210 of the profiled nose 208 allows the protective shoe 204 to more readily be guided under and along a cast 212, between the cast 212 and a body portion 214 or a patient.

The protective shoe 206 shown in FIG. 28 also incorporates a profiled nose 216. However, in this specific embodiment the nose 216 is defined by an upper and a lower tapered surface 218, 220. Thus, the nose 216 shown in FIG. 28 is in the form of a wedge which allows the protective shoe 206 to be more readily inserted between two layers of a cast 222, in order to separate the layers. For example, and as shown in FIG. 28, the protective shoe 206 may be inserted between a soft wadding or bandage layer 224 and a rigid layer 226 of the cast 222, with the cutting means (not shown) of the cast-cutter being used to cut through the rigid layer only.

Figure 29:
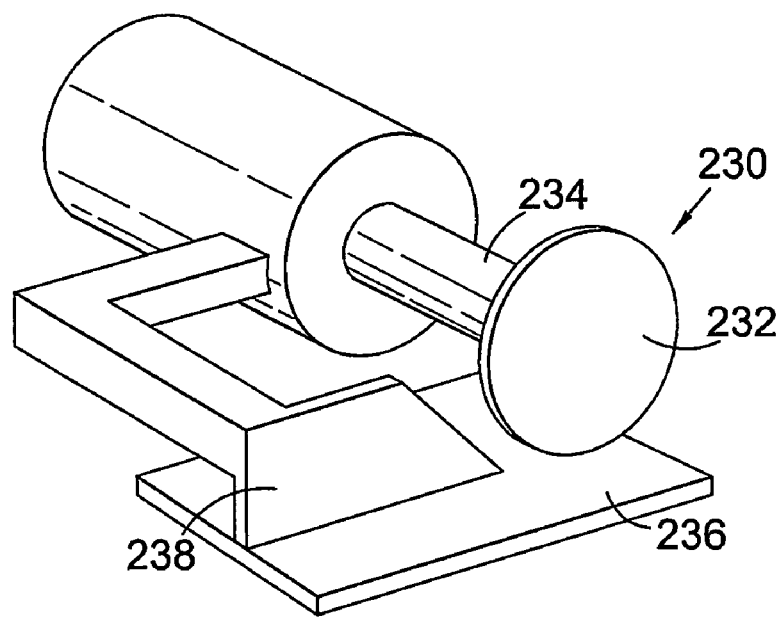
FIG. 29 shows an alternative embodiment of cutting means and protective shoes in accordance with an aspect of the present invention.

An embodiment of a cutting means 230 of a cast-cutter in accordance with an aspect of the present invention is shown in FIG. 29. While the various arrangements described above involve cutting means adapted to cut a cast material using a shearing action, the cutting means 230 of FIG. 29 is adapted to cut a cast material using an abrading action. The cutting means includes a cutting disc 232 mounted on a shaft 234. Although not specifically shown, the disc 232 and shaft 234 may be secured by any suitable means to the body of a cast-cutter, such as that shown in FIG. 1. The cutting disc may be adapted to rotate or oscillate on the shaft 234 in order to effect cutting of a cast.

A protective shoe 236 for use in combination with the cutting means 230 is also shown in FIG. 29. The protective shoe 236 may be secured to the body of a cast-cutter via a connecting member 238 which is sized and arranged to pass through any slot or channel or the like created in a cast by the cutting disc 232. Thus, the protective shoe 236 may be located under and translated along the length of a cast to protect the skin of a patient from injury by the cutting disc 232.

Figure 30:
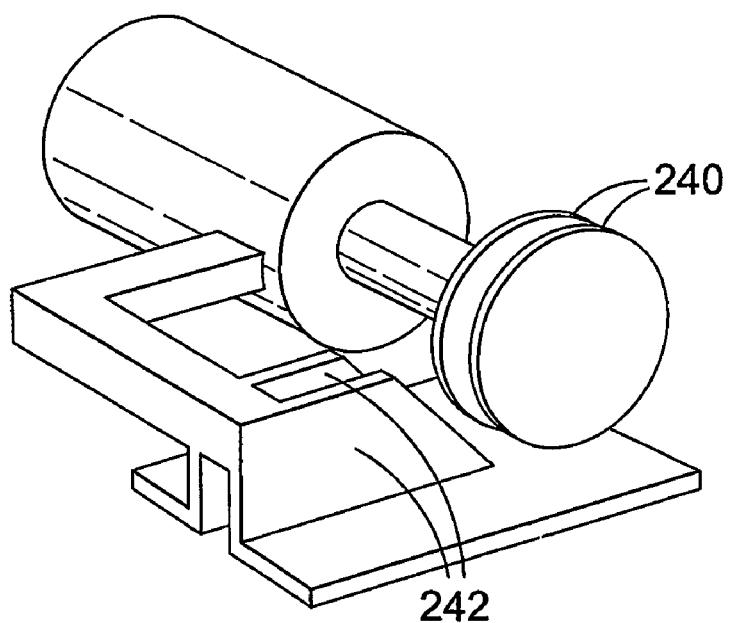
FIG. 30 shows two cutting discs along with two connecting members aligned with a respective disc.

A similar arrangement is shown in FIG. 30 with the exception that two cutting discs 240 are provided, along with two connecting members 242 aligned with a respective disc 240. Thus, in use, the cutting discs 240 form a strip of cast material therebetween, which strip of cast material is free to pass between the connecting members 242, thus preventing any blockage.

Figure 31:
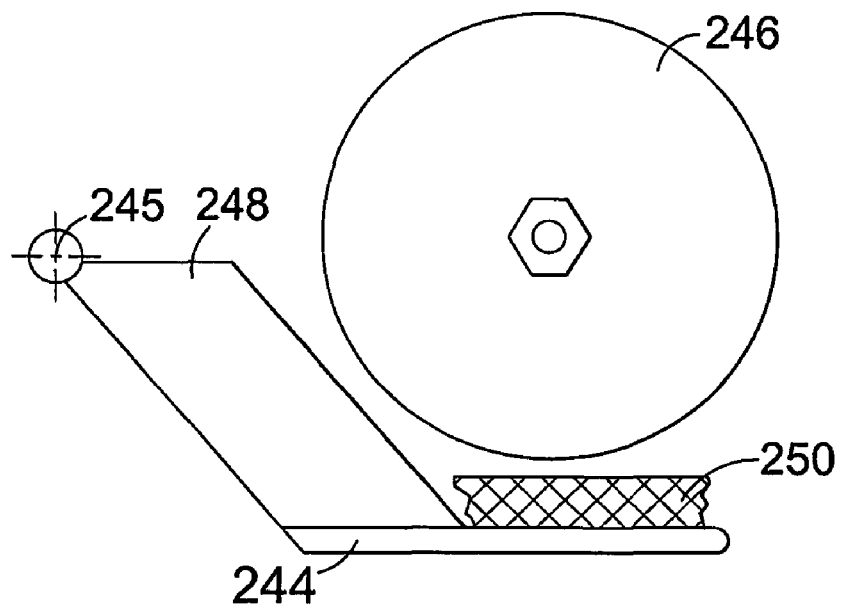
FIG. 31 is a side view of an alternative arrangement of a protective shoe for use in particular with a cutting disc.
Figure 32:
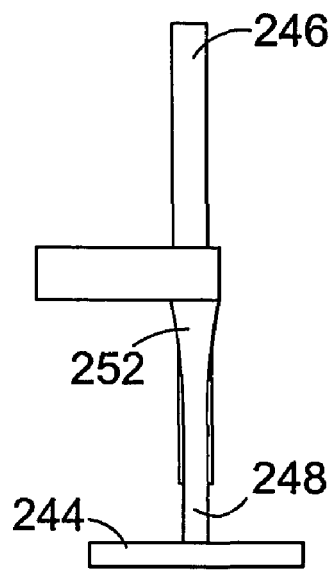
FIG. 32 is a front view of the arrangement of FIG. 31.

Reference is now made to FIGS. 31 and 32 in which there is shown an alternative arrangement of a protective shoe 244 for use in particular with a cutting disc 246. The protective shoe 244 is pivotally mounted on a body (not shown) of a cast-cutter at pivot point 245 by way of a connecting member 248, one end of which is fixed to the protective shoe 244 and the other end of which is pivotally mounted on the body at point 245. This arrangement allows the distance between the protective shoe 244 and the cutting disc 246 to be varied in accordance with the thickness of the cast 250 to be cut, for example. Additionally, pivotally mounting the protective shoe 244 on the body of a cast-cutter will allow the cutting disc 246 to be removed from the cast material 250 being cut, without having to retract the protective shoe 244 from underneath the cast.

A side view of the protective shoe 244, connecting member 248 and cutting disc 246 of FIG. 31 is shown in FIG. 32. As shown, the connecting member 248 includes a widened portion 252 which in use assists to spread apart the cast which is being cut by the disc 246 in order to minimise or substantially prevent the disc 246 from becoming trapped within the cast material.

It should be understood that the embodiments hereinbefore described are merely exemplary of the present invention and that various modifications may be made thereto without departing from the scope of the invention. For example, any fixed portion of the cutting means may be mounted separately from the protective shoe, for example on the connecting member which connects the protective shoe to the body portion of the cast-cutter. Additionally, a collector may be provided which collects and retains the cuttings of cast which are removed during operation. The collector may be mounted on the cast-cutter or alternatively may be located separately therefrom. Additionally, extraction means may be provided to assist in collecting the portions of cast which have been removed, along with any dust. The extraction means may be a vacuum unit or the like.

Furthermore, the cast-cutter may be powered by a battery pack or the like mounted on or in the body of the cast-cutter.

In the embodiments shown which operate to cut a cast material by a shearing action, the cutting means operates by relative reciprocal or pivotal motion between the first and second cutting portions. However, cutting may be effected by a relative rotational motion or the like. Additionally, the cutting means, in use, may also assist in moving the cast-cutter along the length of the cast.

The cast-cutter may additionally comprise control means in association with sensing means which allow the cutting means of the cast-cutter to only be activated when a cast section is located between the first and second cutting portions.

Figure 33:
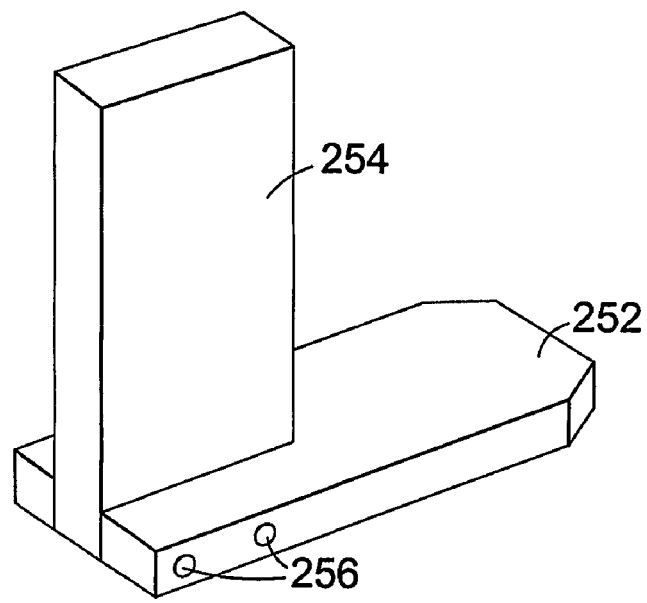
FIG. 33 is a diagrammatic representation of a removable protective shoe in accordance with an embodiment of a present invention.
Figure 34:
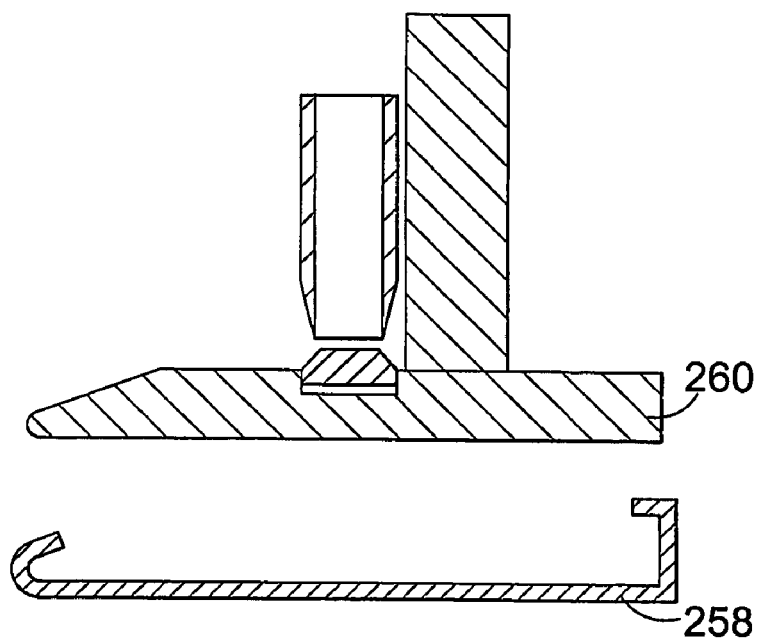
FIG. 34 is a diagrammatic representation of a cover for use with a protective shoe in accordance with an embodiment of the present invention.

Furthermore, the protective shoe of the cast-cutter may be removable to allow replacement. A general representation of this feature is shown in FIG. 33 which shows a protective shoe 252 secured to a connecting member 254 via suitable fixings 256 which allow the protective shoe to be removed and replaced as required. Alternatively, a cover 258, shown in FIG. 34, may be secured over the protective shoe 260 such that only the cover 258 need be replaced, for example when the cast-cutter is to be used on different patients.

A number of alternative embodiments have been described above in accordance with aspects of the present invention. It should be appreciated that these various embodiments may be used in various combinations and are not limited for use as specifically shown and described.

The invention claimed is:

1. A cast-cutter for use in removing a cast from a patient, the cast-cutter comprising:
a housing;
a protection member rigidly fixed to said housing via a connection member, one end of said connection member integrally formed with said protection member and the other end of the connection member coupled to said housing, said protection member comprising a substantially planar skin-contact surface; wherein said skin-contact surface is wider than said connection member in a direction substantially perpendicular to a cutting plane;
a cutting assembly configured to cut along the cutting plane through a cast arranged in a cast plane, the cast plane substantially perpendicular to the cutting plane, said cutting assembly comprising:
a stationary first portion integrally formed with said protection member, and
a moveable second portion, supported for pivotal motion relative to the first portion,
wherein each portion comprises a single cutting edge configured to cooperate to cut along the common cutting plane;
said protection member positioned on one side of the cast plane to be positioned between the cast being operated upon by the cutting assembly and a patient to protect the skin of the patient; and
an electric drive disposed within said housing and drivingly connected to said second portion to pivot said second portion relative to said first portion through an arcuate path which moves the single cutting edge of the second portion through the cast plane from one side thereof and causes a cast positioned between the cutting edges of the first and second portions in the cast plane to be pressed against the single cutting edge of the stationary first portion, such that the respective single cutting edges of the first and second portions effect cutting through the cast plane from opposing sides by a shearing action.

2. A cast-cutter as claimed in claim 1, wherein the cutting assembly is adapted for removing a strip of material from the cast.

3. A cast-cutter as claimed in claim 1, wherein said first portion and protection member are releasably coupled to the housing.

4. A cast-cutter as claimed in claim 1, wherein a leading edge of the second portion of the cutting assembly is chamfered.

5. A cast-cutter as claimed in claim 1, wherein the first portion defines an aperture which is chamfered at one side.

6. A cast-cutter as claimed in claim 1, wherein said cutting assembly is adapted to remove continuous strips of material from a cast and the first portion of the cutting assembly comprises a strip exit to allow a strip of the cast which is being removed to pass therethrough.

7. A cast-cutter as claimed in claim 6, wherein the strip exit comprises tapered sides, which taper outwards, away from the aperture of the first portion.

8. The cast-cutter of claim 1, wherein the protection member further comprises an integral front guard, said front guard extending across the cutting plane, such that the stationary portion cutting edge is located between the front guard and the connection member.

9. The cast-cutter of claim 1, wherein the protection member further comprises a profiled nose, said profiled nose comprising an upper tapered surface proximal to the cast plane.

* * * * *